United States Patent [19]

McGredy, IV

[11] Patent Number: Plant 6,713

[45] Date of Patent: Apr. 4, 1989

[54] FLORIBUNDA ROSE CV. MACREXY

[75] Inventor: Samuel McGredy, IV, Aukland, New Zealand

[73] Assignee: Bear Creek Gardens, Inc., Medford, Oreg.

[21] Appl. No.: 116,731

[22] Filed: Oct. 28, 1987

[51] Int. Cl.[4] ..... A01H 5/00

[52] U.S. Cl. ..... Plt./26

[58] Field of Search ..... Plt./26

*Primary Examiner*—Robert E. Bagwill

*Attorney, Agent, or Firm*—Majestic, Gallagher Parsons & Siebert

[57] ABSTRACT

This invention relates to a new and distinct variety of floribunda Rose cv. Macrexy, cultivated for garden decoration and having large trusses of soft, creamy pink flowers which bloom all through the growing season.

1 Drawing Sheet

This invention relates to a new and distinct variety of rose plant cv. Macrexy, of the floribunda class. The plant is a hardy outdoor seedling of the short bush type, cultivated for garden decoration. It was bred by Samuel McGredy, IV (a citizen of the United Kingdom residing at Auckland, New Zealand) under conditions of careful control and observation, and has as its seed parent the miniature rose cv. Macnewing (unpatented) and as its pollen parent, the floribunda rose cv. Traumerei (unpatented).

The new rose cv. Macrexy is particularly distinguishable from other presently available commercial rose cultivars by the following combination of characteristics: Macrexy is a garden variety, very compact and upright in growth habit, remaining under 3 feet in height; and it is extremely floriferous with large trusses of soft creamy pink color flowers. The plant holds its distinguishing characteristics through succeeding propagations by budding.

The new variety cv. Macrexy may be distinguished from its seed parent, Macnewing by the following combination of characteristics: Whereas Macnewing is a miniature rose, Macrexy is a floribunda rose; the blooms of Macnewing are approximately 1 inch in diameter, whereas those of Macrexy are about 2.5 to about 3 inches in diameter; and whereas the blooms of Manewing are a pale pink; those of Macrexy are of a deeper pink color, essentially as described herein.

The new variety may be distinguished from its pollen parent Traumerei by the following combination of characteristics: The bloom color of Traumerei is salmon pink, whereas that of Macrexy is predominantly pink with only a hint of orange, essentially as described herein; the bloom size of Traumerei is larger than the bloom size of Macrexy whereas the bloom clusters of Macrexy are larger in size than the bloom clusters of Traumerei.

The accompanying drawing illustrates the new variety in color as grown at Shafter, Calif. and shows the flowering thereof from bud to full bloom. Throughout this specification, color names beginning with a small letter signify that the name of that color as used in common speech is aptly descriptive. Color names beginning with a capital letter designate values based upon the R.H.S. Colour Chart of The Royal Horticultural Society of London, England.

The descriptive matter which follows pertains to roses of the new variety grown outdoors at Shafter, Calif., and is believed to apply generally to roses grown under similar conditions of soil and climate elsewhere. Plants and flowers of the new variety grown in other locations may vary in slight detail according to the climatic, soil and cultural conditions under which the variety is grown.

FLOWER

The new variety is extremely floriferous with large trusses of soft, creamy pink color flowers. It usually bears 7–9 flowers to a stem. Flowers are borne in irregular, rounded clusters on stems of normal strength which are short to medium in length for the class. Outdoors, the plant blooms very abundantly and nearly continuously during the growing season. Flowers have a moderate tea fragrance.

BUD

The peduncle is short to average in length for the class, of average caliper, and strong. Its surface is smooth, with some stipitate glands. Bud color is between Green 143A and Green 143B, irregularly overlayed with between Greyed-Purple 184B and Greyed-Purple 184D.

Before the calyx breaks, the bud is of medium size for the class, of medium, length, and pointed, ovoid to ovoid globular in form with a conspicuous neck. There are few foliaceous appendages and stipitate glands on the surface of the bud, with slender entire foliaceous parts extending beyond the tip of the bud and equal to about one quarter of its length.

As the calyx breaks, bud color is near Red 50B where sunlight reaches the petals and approximately Red 51B where the petals are shaded by the sepals.

The inner surface of the sepals has a wooly tomentum; margins are lined with stipitate glands and hairs.

As the first petal opens, the bud is average in size for the class, of medium length, and ovoid to globular in form. The color of the outside surface of the newly opening petals is about Red 50D near the base of the petal and about Red 50C near the margin of the petal. The inside surface of newly opening petals is near Red 50C over the entire surface of the petal.

The bud opens up well and is not prevented from opening in hot, wet or dry weather.

BLOOM

When fully open, the bloom is average in size for the class, averaging from about 2½ to about 3 inches in diameter. Petalage is double, averaging about 39 to about 51 petals arranged regularly; there are about 3 to about 5 petaloids present. When half open, the bloom is somewhat flat-topped, and the petals are somewhat cupped with petal edges flat. When fully open, the bloom is flat to cupped, with petal edges slightly rolled outward.

The petals are of moderately heavy substance and of medium thickness, with insides and outsides satiny. The outside petals are broadly obovate in shape, with flat to rounded apices, and usually are without notches. The intermediate petals are broadly obovate in shape, with rounded to flattened apices, and usually with 1 to 2 notches. The inner petals are obovate, sometimes scalloped, with flat apices, and usually with zero to 2 notches. Petal colors may be modified by being tinted with other colors.

The paragraphs immediately following describe the color values observed in a newly opened flower from a plant of the new variety grown outdoors in Shafter, Calif. during May of 1987.

The outside surface of the outer petals is near Red 55B, with a small basal area near Red 45C. The inside surface of the outside petals is a soft pink, between about Red 45D an about Red 49A with a yellow green basal area near Yellow-Green 154D.

The outside surface of the intermediate petals is between about Red 55B and about Red 55C, with a small basal area near Yellow-Green 154C. The inside surface of the intermediate petals is near Red 49B, with a yellow-green basal area (about 1 mm in diameter) near Yellow-Green 154B.

The outside surface of the inner petals is almost entirely between Red 55B and Red 55C. The inside surface of the inner petal is near Red 39B, with a small basal area near Yellow-Green 145B.

The paragraphs which immediately follow describe the color values observed in a bloom which had been open three days outdoors during May.

The outside surface of both the outer and inner petals is between about Red 55A and about Red 56D in color, with a small basal area near Yellow-Green 154D. The inside surface of both the outer and inner petals is near Red 50D in color, with a small basal area near Yellow-Green 154D.

The general color effect of the newly opened flowers is a very smooth and uniform creamy pink, with just a hint of orange. The general color effect of a flower open for three days is a lighter pink, still uniform in color, but without evidence of any orange color.

Petals usually drop off cleanly and are not particularly affected by hot or cold weather. Flowers on garden plants last 5 or more days in May. Cut flowers from plants grown outdoors in May last from 6 to 7 days when kept at living-room temperatures.

REPRODUCTIVE ORGANS

Stamens are average in number and arranged regularly about the pistils; a few are mixed in with petaloids. The filaments are medium in length and most bear anthers. Anthers are medium to large in size and all open at approximately the same time. Anther color is near Yellow-Orange 21C when immature and near Yellow-Orange 21B at maturity. Pollen is present in moderate amounts. Pollen color is near Yellow-Orange 20A.

Pistils are average in number for the class (approximately 30). Styles are even to uneven, of average length and caliper and are somewhat bunched. Stigma color is between Green-Yellow 1C and Green-Yellow 2C. Ovaries are usually enclosed in the calyx although a few may protrude from the calyx.

Hips are average in length, globular in shape, and bright orange in color, near Orange-Red 33A; hip walls are smooth, thick and fleshy.

The sepals are permanent, spear-shaped and of medium length. Outside sepal color is a dirty orange, near Greyed-Orange 170C.

Seeds are average in number, (about 15 to 20) and are of medium size.

FOLIAGE

The compound leaves are borne in moderate quantities, and usually comprises 3 to 5 medium-sized, moderately heavy and semi-glossy leaflets. The leaflets are nearly oval in shape, with acute apices and obtuse bases; their margins are doubly serrate.

The upper surface of the mature foliage is between Green 137A and Green 137B in color; its under surface is between Green 138B and Green 139C. The upper surface of the young foliage is a bronze green, near Green 144A suffused with near Greyed-Orange 173A. The under surface of the young foliage near Greyed-Purple 148A.

The rachis is light to average in size and bears some stipitate glands on the edges. Its upper side is grooved and its underside is sparsely prickly and has stipitate glands.

Stipules are short in length for the class, narrow to medium in width, and have short points which usually turn out at an angle of less than 45°.

The plant displays a greater than average resistance to mildew, rust and blackspot as compared to other cultivars now in commerce when grown under comparable conditions in Shafter, Calif., U.S.A.

GROWTH

Plants of the new variety are short to medium in height (remaining under about 3 feet tall), have a very compact and upright growth habit and are much branched. Plant growth is very vigorous. Canes are of medium caliper for the class.

The main stems are between Green 143A and Green 143C in color. They bear few to several large prickles, of medium length for the class, which are hooked downwardly. The prickle base is narrow and of medium length. Large prickle color is near Yellow-Green 153D. There are no small prickles or hairs.

Branches are between Green 143A and Green 143C in color. They bear several large prickles, of medium-length for the class, which are hooked slightly downward. The prickle base is short and narrow. Large prickle color is near Yellow-Green 153C. There are no small prickles or hairs.

New shoots are between Green 143A and Green 143B in color. They bear few large prickles of medium length for the class, which are almost straight and hooked slightly downward. The prickle base is short and narrow. Prickle color is near Yellow-Green 153D. There are no small prickles or hairs.

I claim:

1. A new and distinct variety of floribunda rose cv. Macrexy, the parts thereof, the variety characterized in that it exhibits a very compact and upright growth habit and remains under 3 feet in height; it is extremely floriferous with large trusses of soft, creamy pink color flowers essentially as described and illustrated herein.

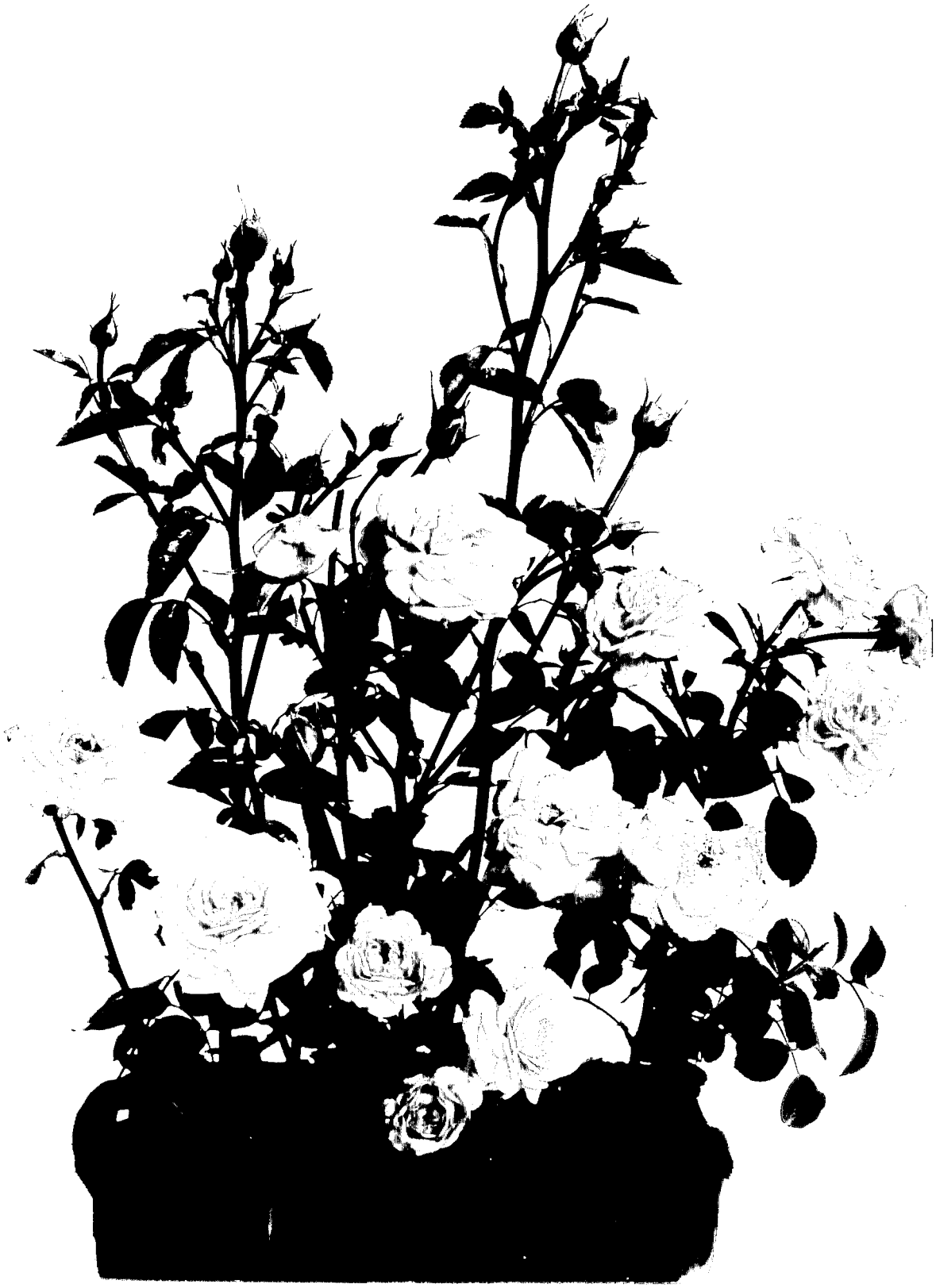

* * * * *